(12) United States Patent
Eckman

(10) Patent No.: US 8,353,962 B2
(45) Date of Patent: Jan. 15, 2013

(54) DUAL COMPOSITION VERTEBRAL DEFECT DEVICE

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 1133 days.

(21) Appl. No.: 11/741,446

(22) Filed: Apr. 27, 2007

(65) Prior Publication Data

US 2008/0015695 A1    Jan. 17, 2008

Related U.S. Application Data

(60) Provisional application No. 60/745,895, filed on Apr. 28, 2006.

(51) Int. Cl.
*A61F 2/44* (2006.01)
(52) U.S. Cl. .................................... 623/17.16
(58) Field of Classification Search ............... 623/17.11, 623/17.16, 17.12–17.15
See application file for complete search history.

(56) References Cited

U.S. PATENT DOCUMENTS

| | | |
|---|---|---|
| 4,349,921 A | 9/1982 | Kuntz |
| 4,545,374 A | 10/1985 | Jacobson |
| 4,936,848 A | 6/1990 | Bagby |
| 4,961,740 A | 10/1990 | Ray et al. |
| 5,258,031 A | 11/1993 | Salib et al. |
| 5,425,773 A | 6/1995 | Boyd et al. |
| 5,522,899 A | 6/1996 | Michelson |
| 5,549,679 A | 8/1996 | Kuslich |
| 5,562,738 A | 10/1996 | Boyd et al. |
| 5,571,189 A | 11/1996 | Kuslich |
| D377,095 S | 12/1996 | Michelson |
| D377,096 S | 12/1996 | Michelson |
| D377,527 S | 1/1997 | Michelson |
| 5,593,409 A | 1/1997 | Michelson |
| 5,607,424 A | 3/1997 | Tropiano |
| 5,609,636 A | 3/1997 | Kohrs et al. |

(Continued)

FOREIGN PATENT DOCUMENTS

EP    1112753 B1    7/2001

(Continued)

OTHER PUBLICATIONS

Scient'x Catalogue, www.scientx.com, 2006.

(Continued)

*Primary Examiner* — Thomas C. Barrett
*Assistant Examiner* — Michael T Schaper
(74) *Attorney, Agent, or Firm* — Panitch Schwarze Belisario & Nadel LLP

(57) ABSTRACT

A vertebral defect device, for insertion between a pair of adjacent lumbar or thoracic vertebrae, includes a frame comprised of a generally rigid first material for structural support strength and rapid fixation. The frame has an upper portion and a lower portion. The upper and lower portions are partially convex, spaced from each other and joined together by distal and proximal supports. A housing is comprised of a second material for minimizing interference with imaging. The housing has a convexly tapered distal end and two generally parallel side walls spaced from each other and extending from the tapered distal end. The housing is coupled to the frame by cooperatively surrounding at least a portion of the frame and oriented such that the side walls are generally perpendicular to the upper and lower portions of the frame when assembled.

24 Claims, 9 Drawing Sheets

U.S. PATENT DOCUMENTS

| | | | |
|---|---|---|---|
| 5,645,596 A | | 7/1997 | Kim et al. |
| 5,653,761 A | | 8/1997 | Pisharodi |
| 5,669,909 A | | 9/1997 | Zdeblick et al. |
| 5,674,296 A | | 10/1997 | Bryan et al. |
| 5,702,449 A | | 12/1997 | McKay |
| 5,776,199 A | | 7/1998 | Michelson |
| 5,785,710 A | | 7/1998 | Michelson |
| 5,888,226 A | | 3/1999 | Rogozinski |
| 5,980,522 A | * | 11/1999 | Koros et al. ............. 623/17.11 |
| 5,984,967 A | | 11/1999 | Zdeblick et al. |
| 6,039,762 A | | 3/2000 | McKay |
| D425,989 S | | 5/2000 | Michelson |
| 6,102,950 A | * | 8/2000 | Vaccaro ................. 623/17.16 |
| 6,113,637 A | | 9/2000 | Gill et al. |
| 6,126,688 A | | 10/2000 | McDonnell |
| 6,136,031 A | | 10/2000 | Middleton |
| 6,174,334 B1 | | 1/2001 | Suddaby |
| 6,193,757 B1 | * | 2/2001 | Foley et al. ............. 623/17.16 |
| 6,231,610 B1 | | 5/2001 | Geisler |
| 6,235,059 B1 | | 5/2001 | Benezech et al. |
| 6,245,108 B1 | | 6/2001 | Biscup |
| 6,270,528 B1 | | 8/2001 | McKay |
| 6,309,421 B1 | * | 10/2001 | Pisharodi ............... 623/17.16 |
| 6,419,705 B1 | | 7/2002 | Erickson |
| 6,425,920 B1 | | 7/2002 | Hamada |
| 6,447,547 B1 | | 9/2002 | Michelson |
| 6,454,805 B1 | | 9/2002 | Baccelli et al. |
| 6,468,311 B2 | | 10/2002 | Boyd et al. |
| 6,478,823 B1 | | 11/2002 | Michelson |
| 6,520,991 B2 | * | 2/2003 | Huene .................... 623/17.11 |
| 6,527,803 B1 | * | 3/2003 | Crozet et al. ............ 623/17.11 |
| 6,558,424 B2 | | 5/2003 | Thalgott |
| 6,582,433 B2 | | 6/2003 | Yun |
| 6,648,917 B2 | * | 11/2003 | Gerbec et al. ........... 623/17.11 |
| 6,852,129 B2 | | 2/2005 | Gerbec et al. |
| 6,855,168 B2 | * | 2/2005 | Crozet .................... 623/17.11 |
| 7,044,972 B2 | | 5/2006 | Mathys, Jr. et al. |
| 7,137,997 B2 | | 11/2006 | Paul |
| 7,503,933 B2 | | 3/2009 | Michelson |
| 2001/0018614 A1 | | 8/2001 | Bianchi |
| 2002/0116009 A1 | * | 8/2002 | Fraser et al. ................ 606/99 |
| 2003/0004576 A1 | * | 1/2003 | Thalgott ................. 623/17.16 |
| 2004/0054412 A1 | * | 3/2004 | Gerbec et al. .......... 623/17.15 |
| 2004/0199251 A1 | * | 10/2004 | McCombe et al. ...... 623/17.11 |
| 2004/0254644 A1 | * | 12/2004 | Taylor .................... 623/17.13 |
| 2005/0004672 A1 | * | 1/2005 | Pafford et al. .......... 623/17.11 |
| 2005/0010290 A1 | * | 1/2005 | Hawkins ................. 623/17.11 |
| 2005/0131539 A1 | | 6/2005 | Kohrs |
| 2006/0206208 A1 | | 9/2006 | Michelson |
| 2007/0038545 A1 | | 2/2007 | Smith et al. |
| 2007/0233247 A1 | | 10/2007 | Schwab |

FOREIGN PATENT DOCUMENTS

| | | |
|---|---|---|
| FR | 2794967 A1 | 12/2000 |
| RU | 1424826 A1 | 9/1988 |
| WO | 9640014 A1 | 12/1996 |
| WO | 9714377 A1 | 4/1997 |
| WO | 97/37620 | 10/1997 |
| WO | 9932054 A1 | 7/1999 |
| WO | 02/80819 | 10/2002 |
| WO | WO2007038545 | 4/2007 |

OTHER PUBLICATIONS

Depraetere, P., et al., Interbody Cages in PLIF Surgery: A Multicentric Report, Journal of Musculoskeletal Research, vol. 2, No. 1 (1998) 9-14.

"Prodisc" Brochure, Spine Solutions, New York, NY.

Helmut D. Link et al., "Link SB Charité Artificial Disc: History, Design & Biomechanics", Spinal Restabilization Procedures. Edited by D.L. Kaech and J.R. Jinkins, 297-298 (2002), Berlin, Germany.

Paul C. McAfee, "Artificial Disc Prosthesis: The Link SB Charité III™", Spinal Restabilization Procedures, edited by D.L. Kaech and J.R. Jinkins, 299-301 (2002) Towson, MD.

"Link SB Charité™ Artificial Disc" Brochure, Maintaining Natural Mobility, Link Spine Group, Branford, Connecticut.

"Prodisc" Brochure, Spine Solutions: The Non-Fusion Technology Company.

"Spine Arthroplasty", Spine Industry Analysis Series, Viscogliosi Bros., LLC, Nov. 2001.

Benezech, J., et al., Integrated Cervical Plate-Cage, 1 page (Admitted Prior Art).

Benezech, J., et al., The PCB, success of the year!, Scient'x News Letter, No. 3, Jan. 2003, 2 pages.

Benezech, J., The origins of the PCB, Scient'x News Letter, No. 6, Apr. 2003, 2 pages.

Search Report, dated Jul. 16, 2009, in related European Patent Appln. No. 09005645.8.

Office Action, dated Jul. 23, 2009, in related U.S. Appln. No. 11/741,200.

Search Report, dated Sep. 12, 2007, in related European Patent Appln. No. 07008690.5.

Office Action, issued Jun. 9, 2010, in U.S. Appl. No. 11/741,200.

Office Action Issued Apr. 15, 2011 in European Application Ser. No. 09005645.8.

\* cited by examiner

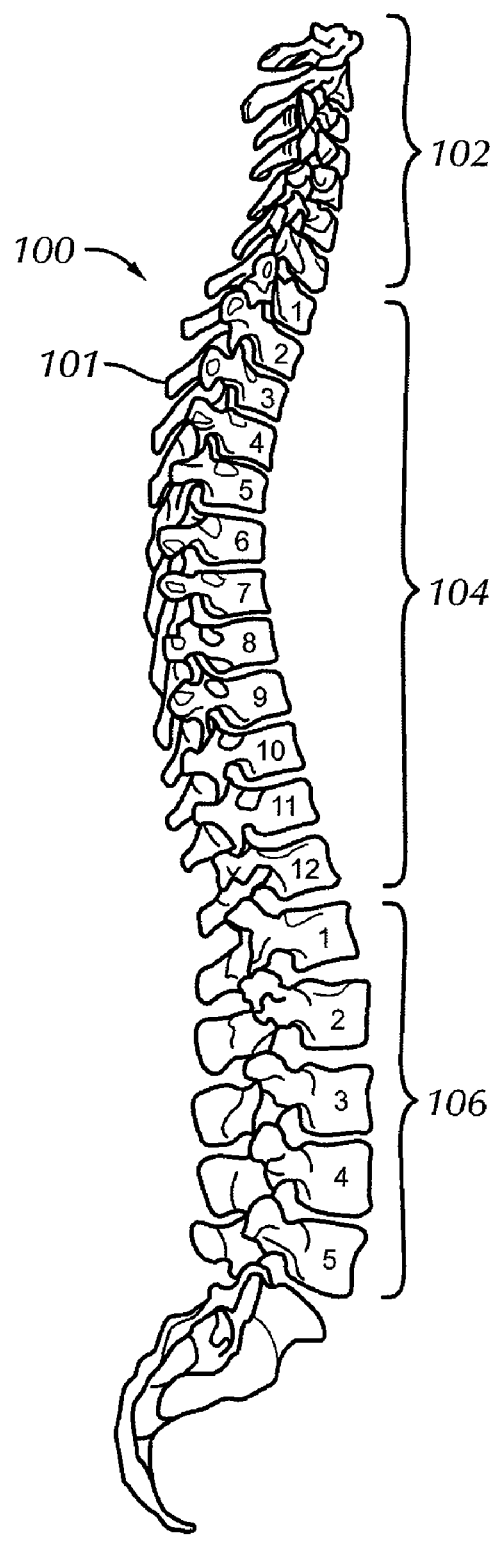
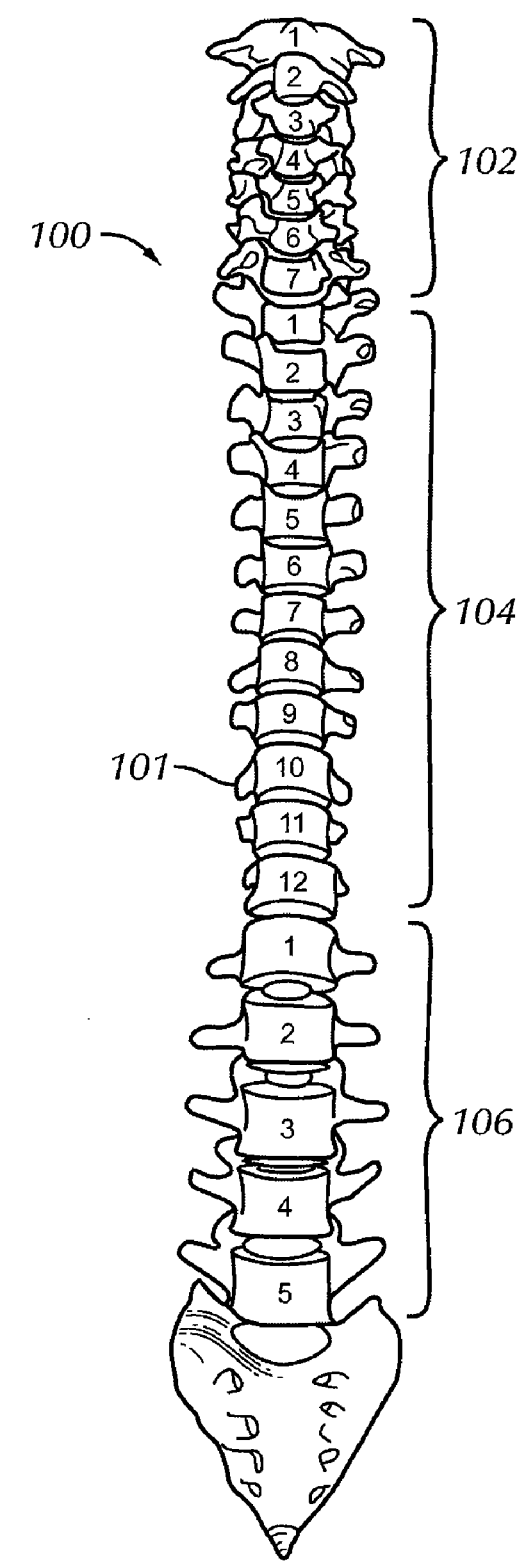
*FIG. 6A*
(Prior Art)
*FIG. 6B*
(Prior Art)

DUAL COMPOSITION VERTEBRAL DEFECT DEVICE

CROSS-REFERENCE TO RELATED APPLICATIONS

This application claims the benefit of U.S. Provisional Patent Application No. 60/745,895 filed Apr. 28, 2006 entitled "Dual Composition Vertebral Defect Device" which is incorporated by reference herein in its entirety.

BACKGROUND OF THE INVENTION

The present invention relates generally to vertebral fixation or defect devices, and more particularly to a dual composition vertebral defect device for insertion into an intervertebral space using minimally invasive techniques, and combining the benefits of support strength and rapid fixation achieved with rigid material, such as titanium, with the advantages of polymeric materials that reduce imaging interference and artifacts.

As shown in prior art FIGS. 6A-10, it is known in the prior art that the spine 100, also known as the spinal column or vertebral column, supports the upper body, allows head, neck, and trunk motion, and includes twenty-four moveable vertebrae 101 including seven cervical vertebrae 102, twelve thoracic vertebrae 104, and five lumbar vertebrae 106, which extend from the skull to the sacrum.

Referring to FIG. 7, with the exception of the first, uppermost cervical vertebra 102, each vertebra 101 has a vertebral body 108, a lamina 110, a spinous process 112, as well as facet structures 114 (which form facet joints), two transverse processes 116, and two pedicles 118, one on each side. Each individual vertebra 101 has a large foramen 120, which forms the spinal canal (not shown) when the vertebrae 101 are in their normal anatomical position forming the spine 100. The spinal cord and major nerve fiber groups pass through and are protected by the spinal canal. A strong fibrous membrane, the dura mater (not shown), also known as the dura, surrounds the spinal cord, nerve fibers, and fluid in the spinal canal.

Referring now to FIGS. 7 and 8, each pair of adjacent vertebrae 101 along with interconnecting soft tissues and an intervertebral disk 128 constitutes a motion segment 122, also known as a functional spinal unit, and the combined motions of many such motion segments 122 constitute overall spinal motion at any one time. The joining of two vertebrae 101 also creates two neuroforaminae 124, also known as intervertebral foraminae, one on each side, each of which is bordered by a facet joint 126 dorsally, a pedicle 118 superiorly, a pedicle 118 inferiorly, and an intervertebral disk 128 ventrally. Each neuroforamina 124 allows passage of large nerve roots (not shown) and associated blood vessels (not shown). The intervertebral disk 128 resides in the space between adjacent vertebral bodies, the intervertebral space 130, also known as the interbody space or disk space. The level of each particular intervertebral space 130 and intervertebral disk 128 is identified by naming the vertebrae 101 superior and inferior to it, for example L 4-5 in the case of the intervertebral space 130 and intervertebral disk 128 between the fourth and fifth lumbar vertebrae 106.

Referring to FIG. 9, each intervertebral disk 128 includes a collection of peripheral concentric rings of strong ligaments known as annular ligaments 132, also known as the annulus, and a softer central area of normally well hydrated material known as the nucleus 134. The annular ligaments 132 are arranged at different angles in alternate layers such that they provide support and stability, resisting excessive vertebral body rotation and axial motion when proper tension is maintained. Although described by some as a cushion, the nucleus 134 is relatively incompressible in a young healthy spine, and thus its major role is to provide support and tension of the annular ligaments 132 to maintain stability while allowing a limited range of motion.

Referring now to FIG. 10, the superior surface and the inferior surface of the lumbar and thoracic vertebral bodies 108 are concave (the shape of the vertebral space 130 shown in phantom). Owing to the shapes of the inferior and superior surfaces of the vertebral bodies 108, the lumbar and thoracic intervertebral spaces 130 and intervertebral disks 128 are biconvex.

Situations arise in which one or more motion segments 122 do not have adequate support or stability, which can lead to pain, deformity, stenosis of spinal canal or neuroforamina, and impairment or loss of nerve function. In some cases, surgical spine fusion is considered. Spine fusion is a process of growing bone between two or more adjacent vertebrae 101 such that the adjacent vertebrae 101 will move only in unison. This process involves placing bone, or material to guide or stimulate bone growth, in proximity to exposed bone of the vertebrae 101, and then allowing time for new bone to grow and form a structurally strong connection, or fusion, between the vertebrae 101. The earliest such procedures took place approximately a century ago, and the procedures have developed over many years, including various attempts to fuse posterior structures of the spine 100 such as the spinous process 112, lamina 110, facet joint 114, and transverse processes 116.

Recently, there has been more interest in fusion involving bone growth directly between adjacent vertebral bodies 101. Large amounts of well vascularized bone are in close proximity, there is a large surface area available, and the inherent compression force applied between vertebral bodies 101 by muscle tension and the upright position of the human body enhances bone formation and strength. The intervertebral disk space 130 has therefore become a major focus in interbody fusion surgery. The disk space 130 is cleared as much as possible, and cartilage and abnormal surface bone, also known as endplate bone, from adjacent vertebral bodies is removed, after which material is placed in the space to promote fusion. However, loose bone fragments do not provide structural support and therefore fusion is often unsuccessful. Structural bone grafts from the patient or donors have been successful, but may give rise to pain and complications if from the patient, and risk of disease transmission if from a donor.

Vertebral defect devices are increasingly used to assist with fusion between vertebral bodies. Such devices are intended to provide support to prevent excessive collapse of space between vertebrae 101 which could result in stenosis of the spinal canal or neuroforamina, progressive deformity, impairment or loss of nerve function, or pain. Such devices also provide at least one compartment to fill with bone, or material which assists in bone growth, in order to maintain close contact with vertebral bone as new bone is encouraged to bridge across the space 130 involved.

Referring to FIG. 7, which shows a single plan view of a vertebra 101, it is known in the art that interbody devices can be inserted from several directions (indicated by arrowed lines) including posterior interlaminar approaches on both sides A, B, transforaminal or partially lateral approaches C, D, anterior approaches E, and straight lateral approaches F.

Efforts have been made to achieve stabilization with vertebral devices having ridges, threads, or grooves on cylinder shaped devices. Anterior approaches (E) allow more access to the disk space, but require more destruction of the annulus. In the lumbar spine 106, bilateral placement of multiple such devices has sometimes been necessary to achieve adequate stability. Cylindrically-shaped devices, inserted through posterior and transforaminal approaches (A, B, C, D) are associated with increased potential for nerve root or dural injury, particularly when drill tubes and reamers are used to prepare the disk space 130 for fusion.

Some cylindrical bone grafts and devices have also been associated with increased subsidence and kyphotic deformities. Subsidence is the sinking of devices or structural bone grafts into adjacent vertebral bodies. Lumbar fusion procedures involving posterior and transforaminal insertion have relied more on impacted devices, which do not provide immediate stabilization except by some degree of distraction, which is naturally lost by any subsidence, and they have been subject to excessive subsidence in some patients. It has been taught in the art that these devices should be inserted bilaterally to offer proper support.

Vertebral devices have been constructed with polymers such as PEEK and carbon fiber/PEEK combinations. Such devices have the advantage of minimal interference with future imaging studies whether by x-ray, CT scan, or MRI scan. Such devices usually have simple implanted metal markers in front and back to allow limited visualization of their position with x-rays or the like. They are made with thick, vertically straight walls to provide support strength, but once they subside a small amount the straight walls offer no effective resistance to excessive subsidence. The surface area provided for fusion is also limited by the thick walls. Polymer material in current use does not allow construction of sharp edges and fixation elements and does not allow for varied shapes which might solve many of the problems with subsidence.

Lumbar surgery is experiencing an evolution to minimally invasive surgery. This trend has led to the need for devices that can be inserted through small portals or working channels, usually through one small incision on one side of the patient's body. In lumbar fusion, vertebral devices should assist with rapid fixation to minimize the need for extensive additional fixation with bone screws, rods, and plates. Surgeons generally prefer posterior approaches for lumbar spine procedures due to the morbidity of anterior approaches, which also causes adhesion of major vessels and makes repeat anterior surgery very dangerous and even life threatening. When posterior lumbar fusion is performed, there is an opportunity to approach the spine 100 through the neuroforamina 124 and insert interbody devices through a small space free of vital structures which is located lateral to the dura in the canal, medial to the large nerve root passing through the neuroforamina 124, and bordered inferiorly or caudally by the pedicle 118 of the vertebra 101 below the involved disk space 130. The distance between peripheral edges of the vertebrae 101 at the disk space 130 is often small so that entry of devices has required considerable bone removal to safely impact devices into the disk space 130. If a device with a distal end of 3 mm or larger in height or transverse dimension is impacted into the disk space 130, it will frequently displace medially or laterally, and involve nerve structures. When working through a small portal or working channel, it is difficult to see this displacement, which makes some devices dangerous in this regard.

Conventional vertebral devices do not lend themselves to be used in minimally invasive surgery because open bilateral surgery is often necessary. When inserting a conventional vertebral device, a distraction tool is used to open the disk space on one side of the spine 100 to allow insertion of the vertebral device on the other side of the spine 100. Alternatively, pedicle screws on one or both sides of the spine 100 may be used with a distraction instrument to spread the disc space open for insertion of one or more vertebral devices.

It is therefore desirable to provide an impacted vertebral defect device designed to achieve rapid fixation while preventing excessive subsidence. The device should reduce the potential for neural injury during insertion, and reduce or eliminate the need for bilateral lumbar pedicle screws. The device should have excellent support strength, but limit the amount of interference with future imaging studies. It is also desirable to provide a device that can be inserted during minimally invasive surgery and placed through an incision and directly into the disk space without manual or mechanical separation of the vertebrae and preferably asymmetrically obliquely across the disk space. It is further desirable for the device to have distinct elements that show its orientation and angulation in the disk space with minimal time and effort using imaging studies, such as with single plane lateral fluoroscopic x-ray.

BRIEF SUMMARY OF THE INVENTION

Briefly stated, the present invention is directed to a dual composition vertebral defect device for insertion between a pair of adjacent lumbar or thoracic vertebrae. The vertebral defect device includes a frame comprised of a generally rigid first material for structural support strength and rapid fixation. The frame has an upper portion and a lower portion. The upper and lower portions are partially convex, spaced from each other and joined together by distal and proximal supports. A housing is comprised of a second material for minimizing interference with imaging. The housing has a convexly tapered distal end and two generally parallel side walls spaced from each other and extending from the tapered distal end. The housing is coupled to the frame by cooperatively surrounding at least a portion of the frame and oriented such that the side walls are generally perpendicular to the upper and lower portions of the frame when assembled.

In another aspect, the invention is directed to a method of installing a vertebral defect device. The method includes the steps of: making an incision in a posterior region of a patient proximate a small gap between a first vertebra and a second vertebra of a spine of the patient, inserting a distal end of a surgical instrument through the small gap between the first and second vertebrae in order to access an intervertebral space between the first and second vertebrae, removing nuclear disk material from the intervertebral space; inserting the vertebral defect device with protective covers, the vertebral defect device having a frame comprised of a rigid first material for structural support strength and rapid fixation and a housing comprised of a second material for minimizing interference with imaging having a convexly tapered distal end, through the small gap, the tapered distal end separating the first and second vertebrae as the vertebral device is inserted into and within a nuclear region of the intervertebral space between the first and second vertebrae, and removing the protective covers to expose an interior of the vertebral defect device and at least one projection and at least one sharpened edge extending from the vertebral defect device.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 6A is a right side elevation view of a human spinal column as is known in the art;

FIG. 6B is a front elevation view of a human spinal column as is known in the art;

DETAILED DESCRIPTION OF THE INVENTION

Figure 1A:
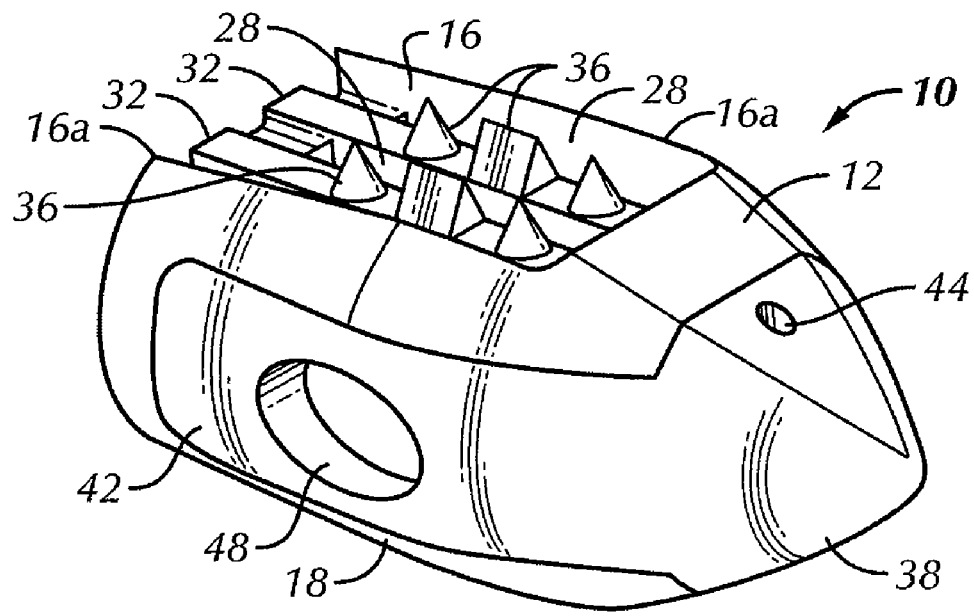
FIG. 1A is a front perspective view of a first preferred embodiment of a dual composition vertebral defect device in accordance with the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of a dual composition vertebral defect device in accordance with the present invention, and designated parts thereof. The words "convex" and "convexly shaped" refer to smooth or continuous surfaces as well as discontinuous surfaces or a plurality of flat planar surfaces which taken as a whole generally represent a convex shape. The phrase "partially convex" means that the feature taken as a whole has a generally convex shape and may include discontinuous or planar surfaces. The terminology includes the words noted above, derivatives thereof and words of similar import. Unless specifically set forth herein, the terms "a", "an" and "the" are not limited to one element but instead should be read as meaning "at least one".

Referring to the drawings in detail, wherein like reference numerals indicate like elements throughout, there is shown in FIGS. 1A-5B two dual composition vertebral defect devices (vertebral defect device or assembled vertebral defect device), generally designated 10, 210, in accordance with first and second preferred embodiments of the present invention for insertion between a pair of adjacent lumbar or thoracic vertebrae 104, 106. Unless specifically set forth herein, the description and method of the first preferred embodiment also applies to the second preferred embodiment.

Referring to FIGS. 1A-4B, the first embodiment of the vertebral defect device 10 includes a frame 12 comprised of a first material. The frame 12 is preferably formed from a machining process, and the least amount of the first material to provide adequate compressive strength and mechanical stability is used. The first material is preferably constructed of surgical grade titanium and is discernable by electromagnetic imaging, such as x-rays and computed tomography (CT) scans, but has minimal interference with magnetic resonance imaging (MRI) scans. The first material may be selected from the group consisting of a biocompatible material such as machined bone, stainless steel, titanium, a cobalt-chrome alloy, a nickel plated metal, a biocompatible alloy, a biocompatible ceramic, a biocompatible polymeric material or a biologically absorbable material. Though the above materials are preferred, any material allowing adequate support strength that could be machined or milled into the shapes and features disclosed below could be used to form the frame 12 without departing from the spirit and scope of the invention.

The frame 12 includes a proximal support 14 located toward the proximal end of the vertebral defect device 10. Upper and lower portions 16, 18 extend generally perpendicularly from the proximal support 14, are permanently joined together by a distal support 22 (described below) and the proximal support 14, and are spaced apart from and generally parallel to each other. The upper and lower portions 16, 18 are at least partially convexly shaped such that the height of the frame 12 is greatest at some location between the proximal and distal ends of the vertebral defect device 10. Though an oval-shape as viewed from the proximal end is shown for the proximal support 14 and it is preferred that the upper and lower portions 16, 18 are convex, it is within the spirit and scope of the present invention that the proximal support 14 and upper and lower portions 16, 18 may have any other shape such as rectangular or diamond and be planar, concave or convex.

The proximal support 14 preferable includes a connector port 14a to temporarily and removably couple with an insertion tool (not shown) as described in further detail below. The connector port 14a is preferably a threaded hole but may also include any other structure for engaging with the insertion tool such as a socket, a detent, a hole a slot or the like.

Figure 1B:
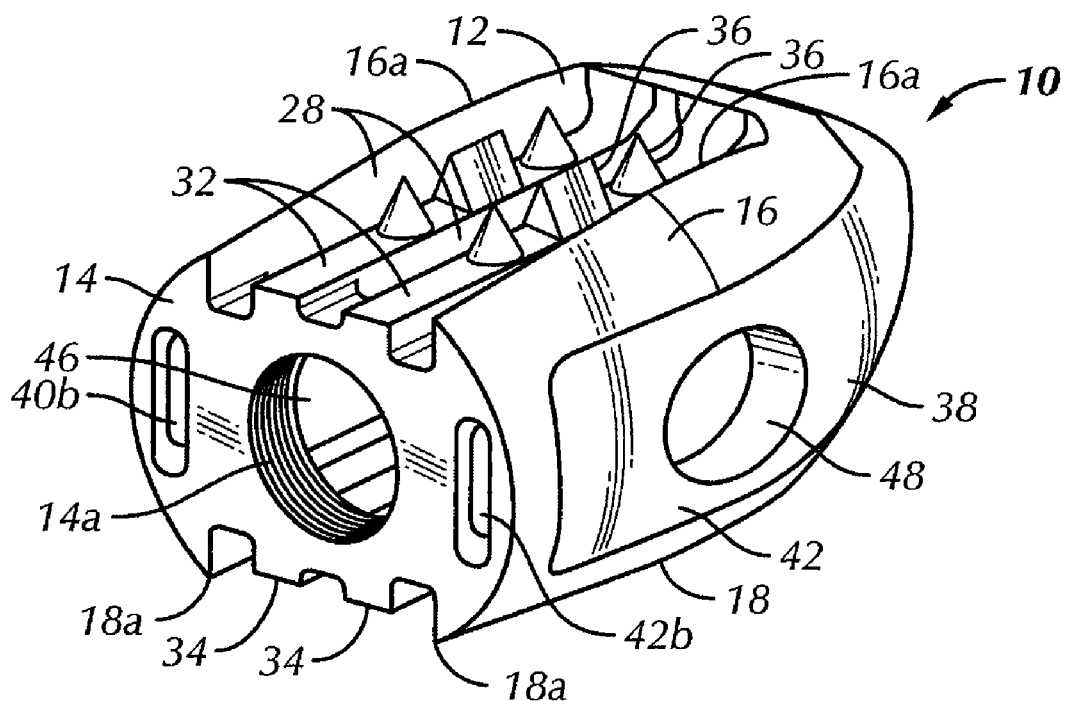
FIG. 1B is a rear perspective view of the vertebral defect device shown in FIG. 1A.
Figure 1C:
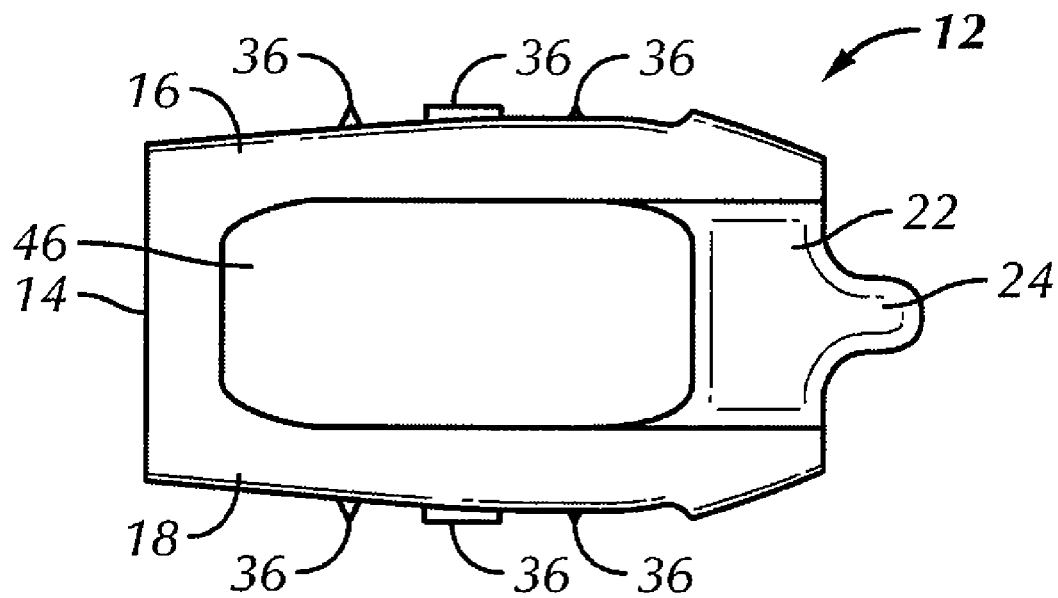
FIG. 1C is a right side elevation view of a frame of the vertebral defect device shown in FIG. 1A.
Figure 2A:
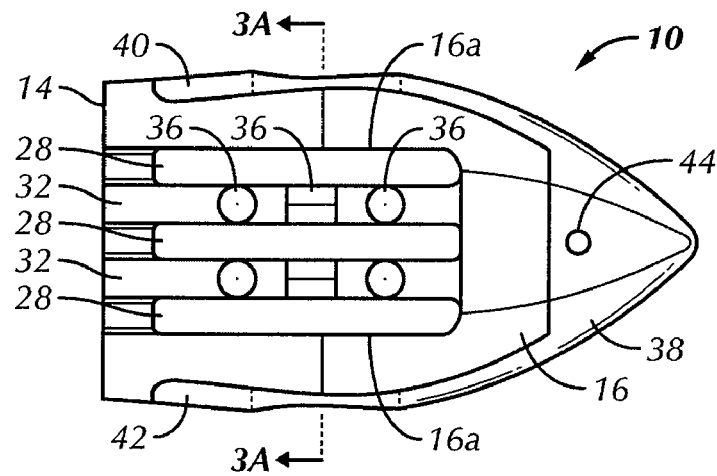
FIG. 2A is a top plan view of the vertebral defect device shown in FIG. 1A.
Figure 2B:
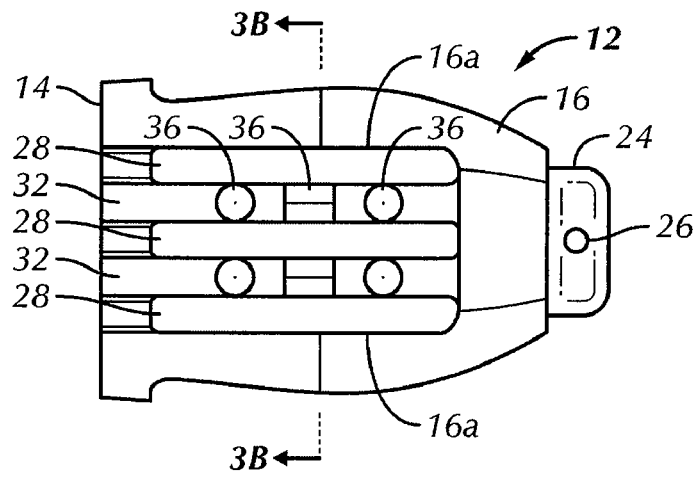
FIG. 2B is a top plan view of the frame shown in FIG. 2A.

Referring to FIGS. 1C and 2B, the closed distal support 22 extends between and supports the distal ends of the upper and lower portions 16, 18. The distal support 22 includes an extension 24. The extension 24 preferably projects distally from the rest of the frame 12. The extension 24 is preferably generally perpendicular to the distal support 22 but it is within the spirit and scope of the present invention that the extension 24 have a different orientation. The extension 24 has a first pin hole 26 extending vertically therethrough.

The upper portion 16 of the frame 12 includes at least one upper opening 28 and preferably three spaced and parallel upper openings 28. The lower portion 18 of the frame 12 has at least one lower opening 30 and preferably three spaced and parallel lower openings 30. The upper and lower openings 28, 30 are configured to allow bone growth into the intervertebral space 130 and are configured to align the vertebral defect device 10 within the intervertebral space 130.

The frame 12 preferably includes at least one upper arch 32 and at least one lower arch 34 spanning the respective openings 28, 30. Preferably, the frame 12 includes two upper arches 32 and two lower arches 34. The upper and lower arches 32, 34 are generally parallel with respect to each other and are spaced apart. The upper and lower arches 32, 34 thicken in the vertical direction toward the proximal and distal ends of the frame 12. The proximal and distal supports 14, 22 help to add strength to the frame 12 and maintain a space between the upper and lower portions 16, 18.

Each of the upper and lower arches 32, 34 preferably includes at least one partially sharpened projection 36. There are preferably three projections 36 on each upper and lower arch 32, 34. The projections 36 are preferably conically or triangularly shaped and project outwardly from the arches 32, 34 by a predetermined distance. Alternatively, the projections 36 may slant toward the proximal end. The projections 36 are disposed at generally equally spaced intervals along each of the respective arches 32, 34. The projections 36 each act as a barb and assist with securely retaining the vertebral defect device 10 in between a pair of vertebrae 101. Once the vertebral defect device 10 is correctly in place and covers 50, discussed below, are removed, the projections 36 penetrate into the bone of the adjacent vertebrae 101 to resist motion of the vertebral defect device 10 with respect to the adjacent vertebrae 101. The upper and lower portions 16, 18 preferably include at least one sharpened edge 16a, 18a respectively. Preferably, there are two sharpened edges 16a, 18a on the upper and lower portions 16, 18 which are parallel and project outwardly from the frame 12 and extend from the proximal end toward the distal end of the frame 12. The sharpened edges 16a, 18a of the upper and lower portions 16 and 18 and the projections 36 provide for rapid fixation of adjacent vertebral bodies thus achieving instant stabilization. Though a combination of conical and triangular projections 36 as shown in FIGS. 1A-4B are preferred, the projections 36 may have any shape and may or may not be included on each arch 32, 34. Any number of projections 36 or sharpened edges 16a, 18a may be made in any number of sizes, shapes, and may be placed in any number of arrangements, so long as the requisite retaining and fixation function is achieved, without departing from the spirit and scope of the invention. In particular, such projections 36 as well as the shape and orientation of the remaining features of the frame 12 are shaped and arranged in ways that impart to the device a readily identifiable unique pattern when imaged after placement in the human body.

A housing 38 comprised of a second material has a convexly tapered closed distal end. The second material is preferably a polymeric material such as PEEK. However, any biologically compatible polymer or other material which does not interfere with imaging could be used. The housing 38 includes two generally parallel sides wall 40, 42 which are spaced from each other and extend from the tapered distal end of the housing 38. The housing 38 is coupled to the frame 12 by cooperatively surrounding at least a portion of the frame 12, preferably at least a portion of the distal support 22 of the frame 12, and may be further secured by use of a pin, screws or any other known fastener. The housing 38 is oriented such that the side walls 40, 42 are generally perpendicular to the upper and lower portions 16, 18 of the frame 12 when the housing 38 and the frame 12 are assembled together.

Figure 1D:
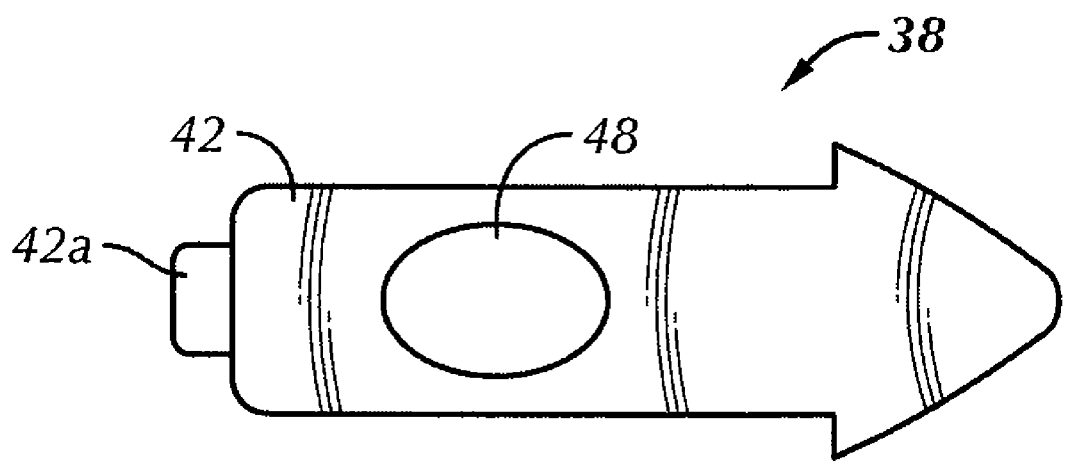
FIG. 1D is a right side elevation view of a housing of the vertebral defect device shown in FIG. 1A.
Figure 2C:
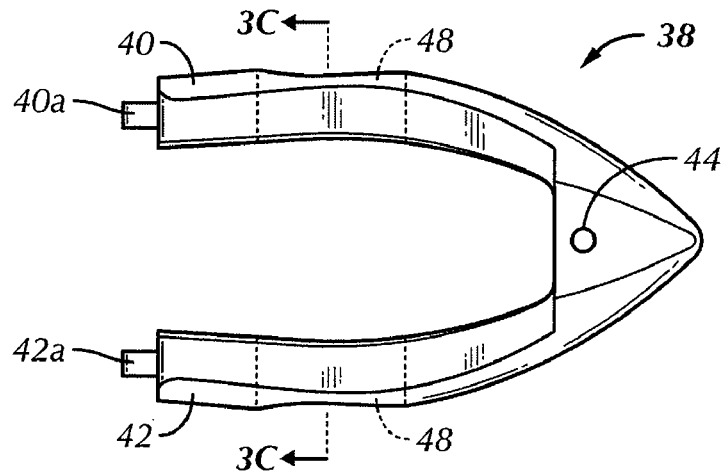
FIG. 2C is a top plan view of the housing shown in FIG. 2A.

Referring to FIGS. 1B, 1D and 2C, the housing 38 is preferably separately constructed from the frame 12 and then assembled by snap-fitting or press-fitting with tabs 40a, 42a extending from the respective side walls 40, 42 and mating with corresponding detents 40b, 42b within the proximal support 14. The tabs 40a, 42a help to keep the side walls 40, 42 from extending laterally or otherwise out of contact with the frame 12. Fasteners (not shown) may be used to further secure the side walls 40, 42 to the frame 12.

Referring to FIGS. 1A-4B, the distal end of the housing 38 includes a second pin hole 44 extending vertically through the distal end. When the vertebral defect device 10 is assembled, the second pin hole 44 is aligned with the first pin hole 26. A pin (not visible) with a length greater than the thickness of the extension 24 and less than the length of the second pin hole 44, is inserted within the first and second pin holes 26, 44 such that the pin retains the housing 38 to the frame 12. Along with the tabs 40a, 42a and or additional fasteners, the pin prevents the housing 38 from inadvertently detaching from the frame 12.

The side walls 40, 42 of the housing 38 may each include a generally circular side opening 48 which extends from the generally hollow interior space 46 through the lateral sides walls 40, 42 to allow for bone growth between the interior space 46 and the intervertebral space 130. Although two generally circular openings 48 are shown, it is understood that more or less than two openings and/or openings of a different shape could be used without departing from the spirit and scope of the invention.

Figure 3A:
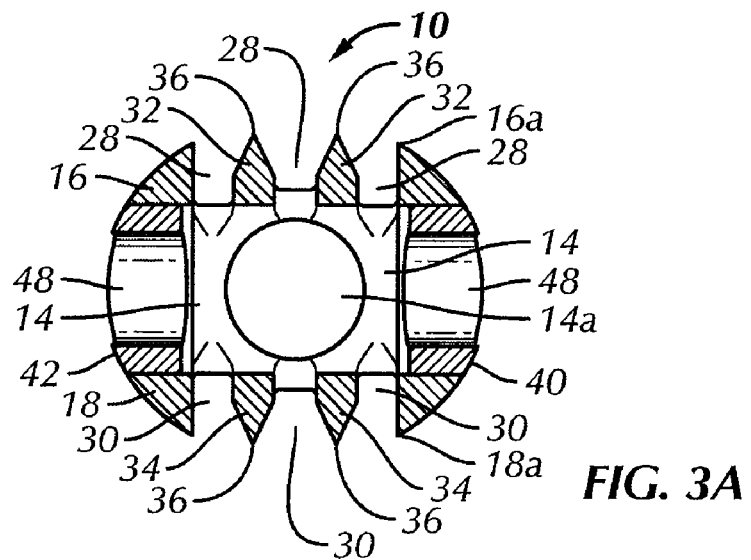
FIG. 3A is a cross-sectional view of the vertebral defect device shown in FIG. 1A taken along line 3A-3A of FIG. 2A.
Figure 3B:
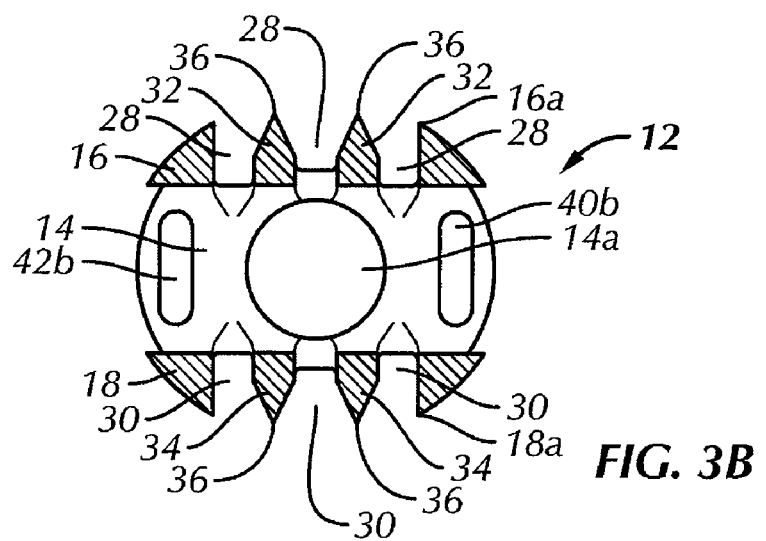
FIG. 3B is a cross-sectional view of the frame shown in FIG. 1C taken along line 3B-3B of FIG. 2B.
Figure 3C:
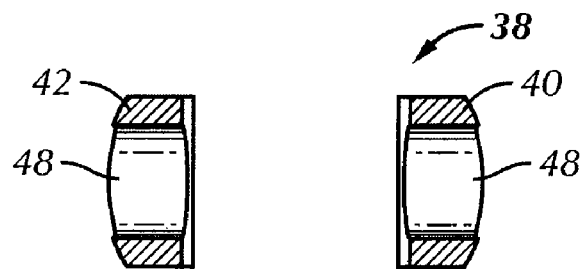
FIG. 3C is a cross-sectional view of the housing shown in FIG. 1D taken along line 3C-3C of FIG. 2C.

Referring to FIGS. 1A and 1B, the assembled vertebral defect device 10 has generally convex features such that the side walls 40, 42 toward the center of the vertebral defect device 10 are the widest part of the vertebral defect device 10 which then taper toward and are flush with the upper and lower portions 16, 18 and also taper toward the proximal and distal ends. A transverse cross sectional view of the assembled vertebral defect device 10, as shown in FIG. 3A, is noncircular even when the covers 50 are inserted. The height of the assembled vertebral defect device 10 is different from the width of the assembled vertebral defect device 10. The vertebral defect device 10 is therefore generally egg-shaped having a generally blunt proximal support 14 and a more pronounced pointed or tapered distal end. For insertion purposes, the distal end of the vertebral defect device 10 has a lesser average radius of curvature than the proximal end. It is preferred that vertebral defect device 10 have a generally egg-shaped or partially convex configuration but it is within the spirit and scope of the present invention that the vertebral defect device 10 have a different shape such as rectangular or having both the proximal and distal end being tapered and having generally flat planar side walls 40, 42.

An outer profile of the vertebral defect device 10 is characterized by a relatively gradual slope, such that the largest transverse dimension (height or width) of the vertebral defect device 10 preferably changes no more than about 2 mm for every 1 mm change in length. Preferably the distal end, in particular, has a slope that changes by no more than 2 mm for every 1 mm change in length. The distal end is relatively small, for example, the height or width preferably less than 2.5 mm in transverse dimension over the terminal 1 mm of the distal end along the longitudinal axis or approximately 15-20% of the maximum height or maximum width of the vertebral defect device 10. However, the distal end should not be so pointed such that it would easily drive through or penetrate the annulus on the opposite side of the intervertebral disk space 130. The size and taper or slope of the distal end of the vertebral defect device 10 is intended to allow it to be impacted into the disk space while providing distraction of the periphery of the vertebral bodies to permit entry into the nuclear center of the disk. This minimizes a need to remove peripheral vertebral bone thus assisting with device retention and helps prevent potential extrusion of the vertebral defect device 10. The vertebral defect device 10 may be dimensioned in accordance with the requirements of specific applications, and other dimensional characteristics of the vertebral defect device 10 are included within the scope of the present invention.

The assembled vertebral defect device 10 preferably includes an interior space 46 generally defined by the shape of the assembled frame 12 and housing 38. The interior space 46 is preferably in communication with the upper and lower openings 28, 30. The interior space 46 may house bone grafts or non-bone matter to promote fusion.

The length of the assembled vertebral defect device 10 as measured between the proximal and distal ends is preferably greater than the width of the vertebral defect device 10 as measured between the lateral sides walls 40, 42 of the housing 38. The length of the vertebral defect device 10 is also preferably greater than the height of the vertebral defect device 10 as measured between the upper and lower portions 16, 18. The length of the assembled vertebral defect device 10 as measured between the distal end of the housing 38 and the proximal support 14 of the frame 12 is preferably approximately 10 to 30 mm. The width of the vertebral defect device 10 as measured between the lateral side walls 40, 42 is preferably approximately 10 mm to 25 mm. The height of the vertebral defect device 10 as measured between the upper and lower portions 16, 18 is preferably approximately 5 to 25 mm.

Figure 4A:
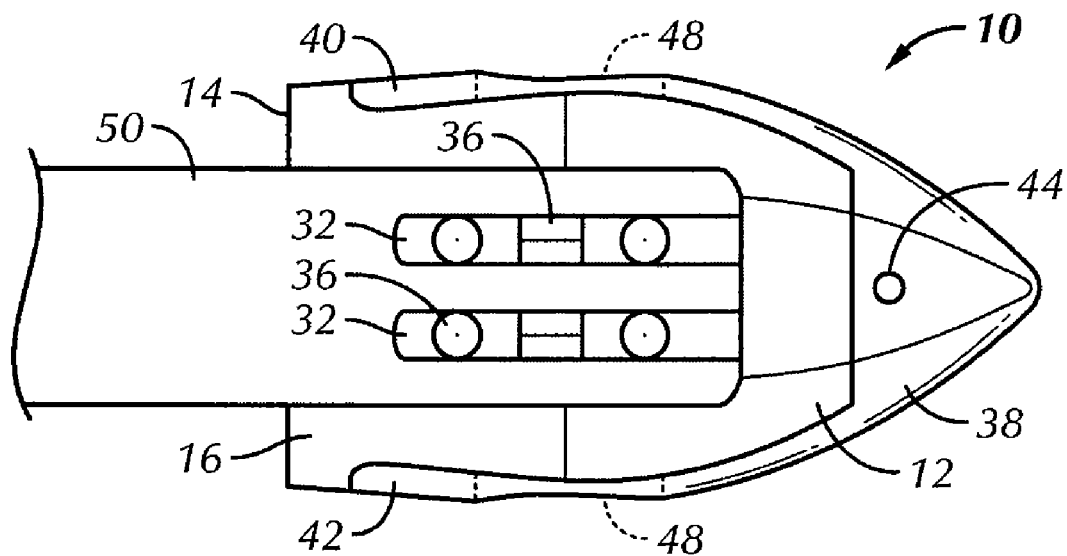
FIG. 4A is a top plan view of the vertebral defect device shown in FIG. 1A with attached protective covers.
Figure 4B:
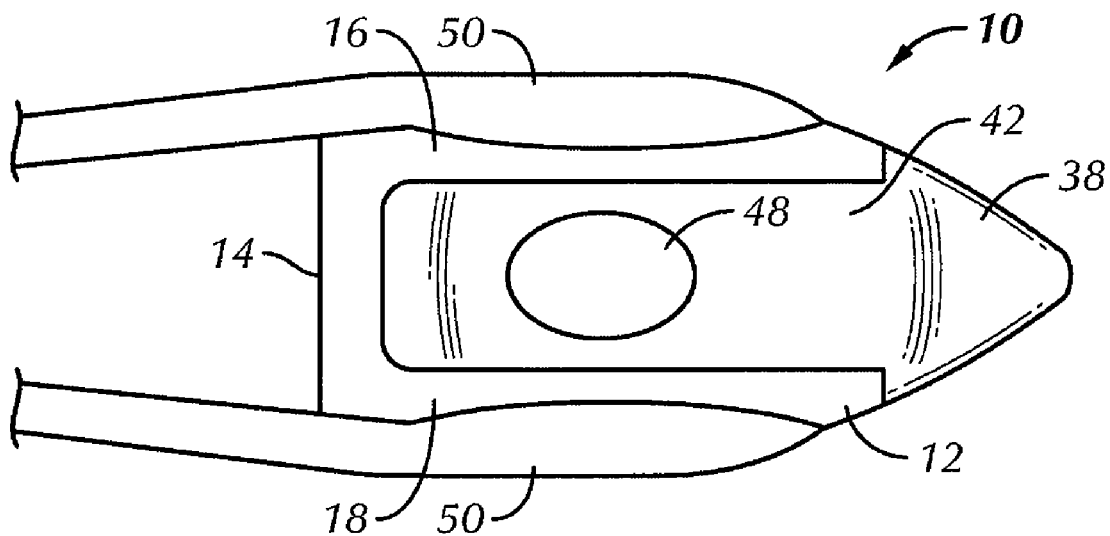
FIG. 4B is a right side elevation view of the vertebral defect device and protective covers shown in FIG. 4A.

Referring to FIGS. 4A and 4B, the vertebral defect device 10 may include one or more protective covers 50. The covers 50 are inserted over the upper and lower openings 28, 30 in the upper and lower portions 16, 18 and cover the upper and lower openings 28, 30, but not the side walls 40, 42 of the housing 38, during insertion of the vertebral defect device 10 and limit the exposure of the projections 36. The covers 50 prevent debris from entering the upper and lower openings 28, 30 and the interior space 46 during insertion of the vertebral defect device 10 and protect nearby anatomic structures, especially the nerve roots, dura, and vessels from injury by the projections 36. During insertion of the vertebral defect device 10 into the disk space using an insertion tool (not shown), two pairs of protective covers 50 are preferably used to cover the upper and lower openings 28, 30. Each of the protective covers 50 is identical and is generally in the form of a smooth surfaced fork. The protective covers 50 are of a thickness that matches the height of the projections 36 above the arches 32, 34 and the sharpened edges 16a, 18a of the upper and lower portions 16, 18 so that preferably no sharp point or surface of the projections 36 or sharpened edges 16a, 18a protrudes beyond the smooth outer surface of the protective covers 50. The vertebral defect device 10 with covers 50 inserted, forms a generally smooth or continuous convex top and bottom.

Figure 5A:
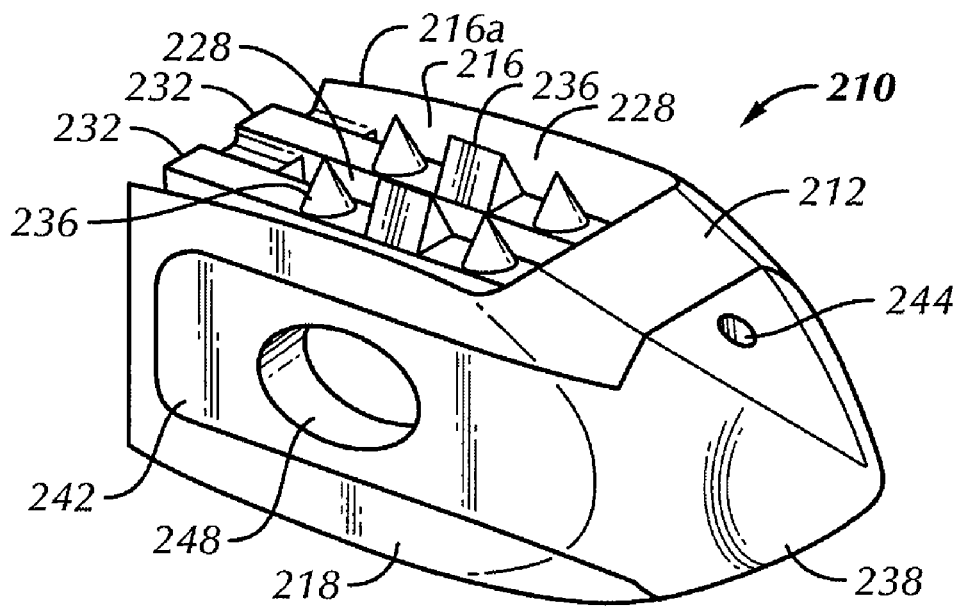
FIG. 5A is a front perspective view of a second preferred embodiment of a dual composition vertebral defect device in accordance with the present invention.
Figure 5B:
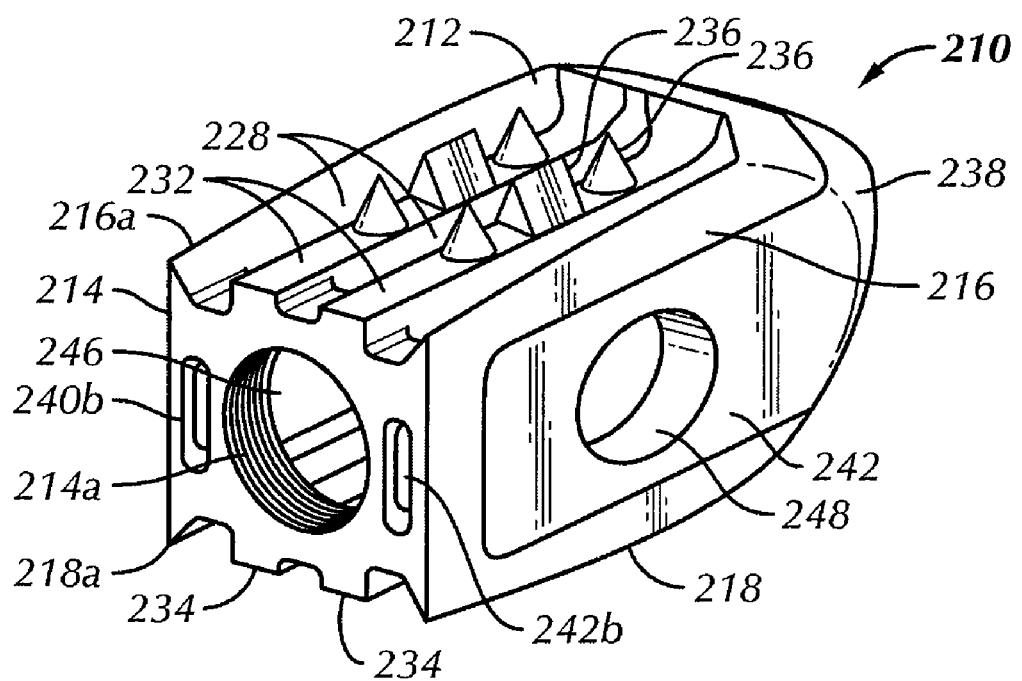
FIG. 5B is a rear perspective view of the vertebral defect device shown in FIG. 5A.

Referring to FIGS. 5A-5B, a second preferred embodiment of the vertebral defect device 210 includes generally planar side walls 240, 242 and has a tapered and convexly shaped distal end. The vertebral defect device 210 of the second preferred embodiment is nearly identical to the first embodiment of the vertebral defect device 10 except that the side walls 240, 242, and lateral sides of the upper and lower portions 216, 218 and proximal support 214 are generally flat or planar and rectangular in shape. Similar numbers indicate similar elements as discussed above for the first embodiment. A discussion of the similar features has been eliminated for convenience only and is not limiting. Though entirely planar side walls 240, 242 are shown, the side walls 240, 242 may be only partially planar such that a portion of the side walls 240, 242 and the lateral sides of the upper and lower portions 216, 218 retain a convex shape. The partially planar sides walls 240, 242 may allow for a more central insertion of the vertebral defect device 210. The upper and lower portions 216, 218 preferably remain partially convex as viewed from the lateral sides similar to the first embodiment. Though a vertebral defect device 210 having at least partially planar side walls 240, 242 is preferred, it is within the spirit and scope of the present invention that the side walls 240, 242 and lateral sides of the upper and lower portions 216, 218 form any shape.

Figure 7:
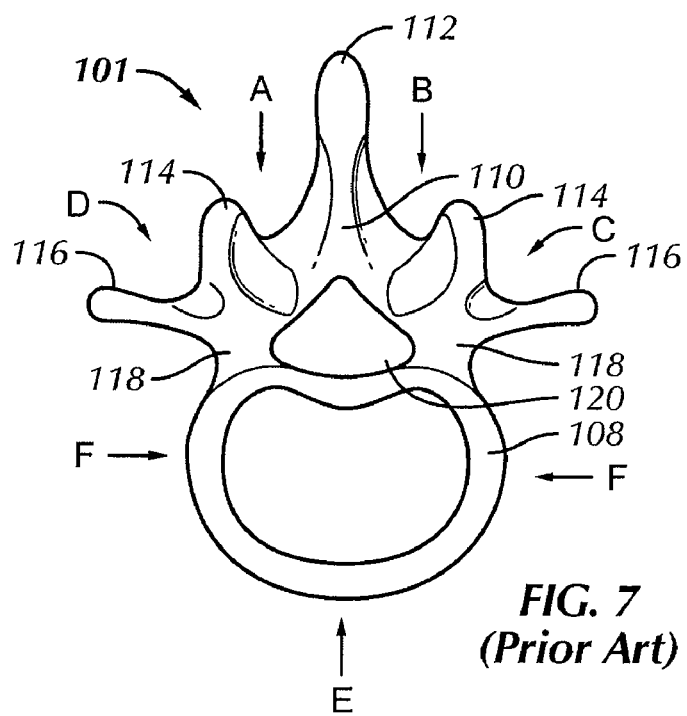
FIG. 7 is a top plan view of a human vertebra as is known in the art.
Figure 8:
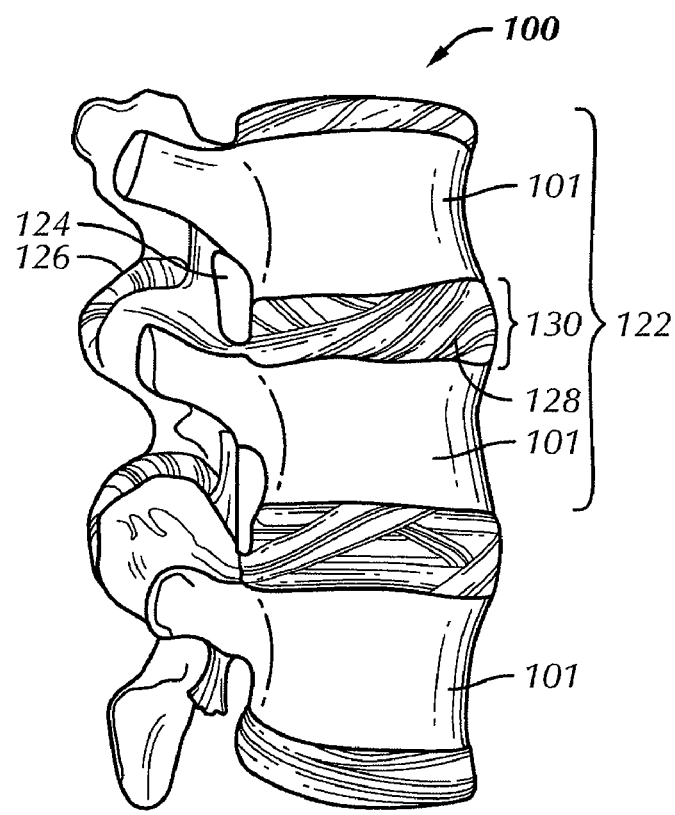
FIG. 8 is a right side elevation view of a portion of the lumbar spine as is known in the art.
Figure 9:
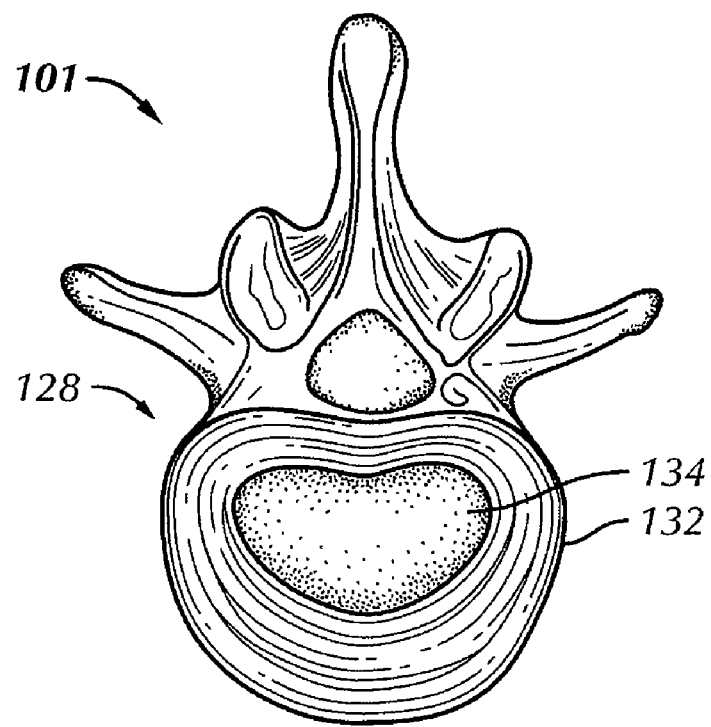
FIG. 9 is a top plan view of a lumbar vertebra and vertebral disk as is known in the art.
Figure 10:
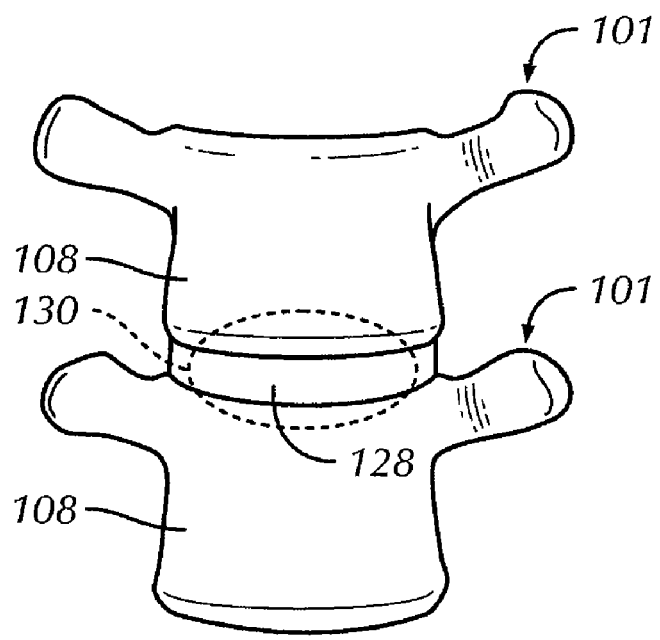
FIG. 10 is a front view of a pair of lumber vertebrae as is known in the art.

During the insertion procedure an incision is made in a posterior region of a patient proximate a small gap between a first vertebra 101 and a second vertebra 101 of a spine 100 of the patient. The incision is preferably between approximately 10 mm to 100 mm in span. The small gap is preferably off-center with respect to the posterior-side of the spine of the patient and proximate to the foraminae 120 of the first and second vertebrae (see directions C and D in FIG. 7) for the first embodiment. Alternatively, the incision may also be generally proximate the midline of the posterior-side of the spine for insertion of the vertebral defect device 210 in a direction A or B. A working channel is then inserted through the incision. A distal end of a surgical instrument is inserted through the working channel between the first and second vertebrae 101 in order to access an intervertebral space 130 between the first and second vertebrae 101. Nuclear disk material 134 is removed from the intervertebral space 130. The vertebral defect device 10, 210 with protective covers 50 is inserted through the small gap. The tapered distal end separates the first and second vertebrae 101 as the vertebral defect device is inserted into and within a nuclear region 134 of the intervertebral space 130 between the first and second vertebrae 101. The positioning of the vertebral defect device 10 is directed by the tilt and angle of the frame 12. The upper and lower portions 16, 18, proximal and distal supports 14, 22 and the various projections 36 help display how the vertebral defect device 10 is positioned within the intervertebral space 130.

Once the vertebral defect device 10 is inserted and properly positioned, the protective covers 50 are withdrawn, allowing penetration of the projections 36 and sharpened edged 16a, 18a into the vertebral bodies 108, and bringing vertebral bone into proximity with bone growth material in the interior space 46. The insertion tool (not shown) remains attached to the vertebral defect device 10 during removal of the covers to maintain position, and is then removed when fixation is achieved.

Though the above method for installing the vertebral defect device 10 is preferred, it is within the spirit and scope of the present invention that additional steps or a different order of the steps presented above be practiced.

The insertion tool (not shown) may be formed of any substantially rigid material, but preferably is formed of titanium, hardened stainless steel, or a biocompatible alloy, composite, polymeric material or the like of sufficient strength. It should be noted that the material of construction of the insertion tool (not shown) could be any material without diverging from the broad scope of the present invention. The protective covers 50 are preferably made of a biocompatible polymer that is strong and somewhat flexible. However, other materials could be used, such as low density metal alloys, without departing from the spirit or scope of the invention.

It will be appreciated by those skilled in the art that changes could be made to the embodiments described above without departing from the broad inventive concept thereof. It is expected that materials science will create polymers that will allow the combination of fixation, support strength, and subsidence prevention which are embodied in the invention and thus new materials could be used in a single composition without departing from the spirit and scope of the present invention. It is understood, therefore, that this invention is not limited to the particular embodiments disclosed, but it is intended to cover modifications within the spirit and scope of the present invention as defined by the appended claims.

I claim:

1. A dual composition vertebral defect device for insertion between a pair of adjacent lumbar or thoracic vertebrae, the dual composition vertebral defect device comprising:
a frame comprised of a generally rigid first material for structural support strength, visibility by x-ray imaging and rapid fixation having an upper portion and a lower portion, the upper and lower portions being spaced from each other and permanently joined together by a distal support and a proximal support, the upper portion of the frame including an upper opening to encourage vertebral fusion and fixation within an intervertebral space and the lower portion of the frame including a lower opening to encourage vertebral fusion and fixation within the intervertebral space, at least one arch spans at least one of the upper opening and the lower opening from the distal support to the proximal support; and
a housing comprised of a second material for minimizing interference with imaging having a convexly tapered distal end for driving into a disk space to provide distraction of a periphery of vertebral bodies and two generally parallel side walls spaced from each other and extending from the tapered distal end, the taper of the distal end having a slope of no more than 2 mm for every 1 mm change in length, the distal end being at least generally closed except for one or more holes for fixation or to promote bone growth, the housing being coupled to the frame by cooperatively surrounding at least a portion of the distal support of the frame and oriented such that the side walls are generally perpendicular to the upper and lower portions of the frame when assembled,
wherein the assembled frame and housing define a hollow interior space that extends from one of the side walls of the housing to the opposing side wall of the housing, wherein the at least one arch extends in a direction at least generally parallel to a longitudinal axis of both the frame and the housing, and wherein the assembled frame and housing are configured to be driven into a disk space between the pair of adjacent vertebrae to provide distraction.

2. The dual composition vertebral defect device of claim 1, wherein the first material is formed at least partially of a biocompatible material selected from the group consisting of: machined bone, titanium, a nickel plated metal, a biocompatible alloy, a biocompatible ceramic, a biocompatible polymeric material and a biologically absorbable material.

3. The dual composition vertebral defect device of claim 1, wherein the frame includes a removable protective cover that covers the upper opening during insertion of the dual composition vertebral defect device within the intervertebral space, wherein the cover does not cover the side walls of the housing, and the combined device and cover form a smooth and convex top.

4. The dual composition vertebral defect device of claim 1, wherein the upper portion of the frame includes two spaced-apart and parallel arches that span the upper opening from the distal support to the proximal support, each arch extending in a direction parallel to the longitudinal axis of both the frame and the housing.

5. The dual composition vertebral defect device of claim 1, wherein the upper opening has a linear sharpened edge that extends an entire length of the upper opening at a lateral side thereof and extends parallel to the longitudinal axis of both the frame and the housing, and wherein the sharpened edge projects outwardly from the device and is formed at least in part by a vertically-extending surface that defines the lateral side of the upper opening.

6. The dual composition vertebral defect device of claim 1, wherein the upper portion of the frame includes at least one sharpened projection extending from the at least one arch.

7. The dual composition vertebral defect device of claim 1, wherein the frame includes a removable protective cover that covers the lower opening during insertion of the dual composition vertebral defect device within the intervertebral space, wherein the cover does not cover the side walls of the housing, and the combined device and cover form a smooth and convex bottom.

8. The dual composition vertebral defect device of claim 1, wherein the lower portion of the frame includes two spaced-apart and parallel arches that span the lower opening from the distal support to the proximal support, each arch extending in a direction parallel to the longitudinal axis of both the frame and the housing.

9. The dual composition vertebral defect device of claim 1, wherein the lower opening has a linear sharpened edge that extends an entire length of the lower opening at a lateral side thereof and extends parallel to the longitudinal axis of both the frame and the housing, and wherein the sharpened edge projects outwardly from the device and is formed at least in part by a vertically-extending surface that defines the lateral side of the lower opening.

10. The dual composition vertebral defect device of claim 1, wherein the lower portion of the frame includes at least one sharpened projection extending from the at least one arch.

11. The dual composition vertebral defect device of claim 1, wherein the upper and lower portions are at least partially convexly shaped such that the height of the vertebral defect device is greatest in an area located between the proximal and distal ends.

12. The dual composition vertebral defect device of claim 1, wherein the proximal support includes a connector port configured to temporarily and removably couple with an insertion tool.

13. The dual composition vertebral defect device of claim 12, wherein the connector port is one of a threaded opening, a socket, a detent, a hole and a slot.

14. The dual composition vertebral defect device of claim 1, wherein the second material is formed at least partially of a biocompatible material selected from the group consisting of: a ceramic, a polymeric material and a biologically absorbable material.

15. The dual composition vertebral defect device of claim 14, wherein the second material is PEEK.

16. The dual composition vertebral defect device of claim 1, wherein each of the sides of the housing includes at least one opening.

17. The dual composition vertebral defect device of claim 1, wherein at least one tab is located proximate the proximal support when the housing and frame are assembled for connecting the frame to the housing.

18. The dual composition vertebral defect device of claim 1, wherein at least one fastener connects the housing to the frame.

19. The dual composition vertebral defect device of claim 1, wherein the assembled vertebral defect device is at least partially convex such that the side walls located proximate the center of the vertebral defect device are the widest lateral part of the vertebral defect device, the side walls taper toward the distal end.

20. The dual composition vertebral defect device of claim 19, wherein the height of the vertebral defect device is different than the width.

21. The dual composition vertebral defect device of claim 1, wherein both the proximal and the distal ends of the vertebral defect device are convexly tapered and the distal end has a lesser average radius of curvature than the proximal end.

22. The dual composition vertebral defect device of claim 1, wherein the side walls are at least partially planar.

23. The dual composition vertebral defect device according to claim 1, wherein the length of the device as measured along the longitudinal axis of both the frame and the housing from the distal end to proximal support of the frame is greater than the width of the device as measured along an axis perpendicular to the longitudinal axis of both the frame and the housing between the sides of the housing and is greater than the height of the device as measured between the upper and lower portions of the frame.

24. The dual composition vertebral defect device according to claim 1, wherein a terminal distal 1 mm of the vertebral defect device measuring along a longitudinal axis has a maximum transverse dimension of 15-20% of the maximum height of the vertebral defect device.

* * * * *